US010255684B2

(12) United States Patent
Osborne et al.

(10) Patent No.: US 10,255,684 B2
(45) Date of Patent: Apr. 9, 2019

(54) MOTION CORRECTION FOR PET MEDICAL IMAGING BASED ON TRACKING OF ANNIHILATION PHOTONS

(71) Applicant: University of Tennessee Research Foundation, Knoxville, TN (US)

(72) Inventors: Dustin R. Osborne, Knoxville, TN (US); Dongming Hu, Knoxville, TN (US); Sang Hyeb Lee, Novato, CA (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 15/174,130

(22) Filed: Jun. 6, 2016

(65) Prior Publication Data

US 2016/0358334 A1 Dec. 8, 2016

Related U.S. Application Data

(60) Provisional application No. 62/171,489, filed on Jun. 5, 2015.

(51) Int. Cl.
*G06K 9/00* (2006.01)
*G06T 7/246* (2017.01)
*G06T 5/00* (2006.01)

(52) U.S. Cl.
CPC ............ *G06T 7/246* (2017.01); *G06T 5/003* (2013.01); *G06T 2207/10104* (2013.01); *G06T 2207/20201* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS

| 7,756,307 | B2* | 7/2010 | Thielemans | G06T 11/005 250/363.08 |
| 8,170,302 | B1* | 5/2012 | Gleason | A61B 6/037 378/4 |
| 8,224,056 | B2* | 7/2012 | Pack | G06T 11/005 378/20 |
| 9,606,245 | B1* | 3/2017 | Czarnecki | G01T 1/2006 |

(Continued)

OTHER PUBLICATIONS

Büther, F., Ernst, I., Hamill, J., Eich, H. T., Schober, O., Schäfers, M., & Schäfers, K. P. (2013). External radioactive markers for PET data-driven respiratory gating in positron emission tomography. European journal of nuclear medicine and molecular imaging, 40(4), 602-614.*

(Continued)

*Primary Examiner* — Bhavesh M Mehta
*Assistant Examiner* — Samah A Beg
(74) *Attorney, Agent, or Firm* — Hunton Andrews Kurth LLP

(57) ABSTRACT

Systems and methods for correcting motion during medical imaging involve using a detector to track annihilation photons produced by one of (i) external emitting sources placed onto a body of a person being imaged or (ii) an object of interest in the body. Motion information is generated based on the tracking. A motion-corrected image is formed from recorded image data, using the motion information.

10 Claims, 8 Drawing Sheets

(56) References Cited

U.S. PATENT DOCUMENTS

| | | | |
|---|---|---|---|
| 2004/0102695 A1* | 5/2004 | Stergiopoulos | G01R 33/56325 600/413 |
| 2005/0123183 A1* | 6/2005 | Schleyer | G06T 5/20 382/131 |
| 2007/0265528 A1* | 11/2007 | Xu | G01T 1/2985 600/426 |
| 2007/0280508 A1* | 12/2007 | Ernst | A61B 5/055 382/107 |
| 2009/0253980 A1* | 10/2009 | Wollenweber | A61B 6/032 600/411 |
| 2010/0054412 A1* | 3/2010 | Brinks | A61B 6/032 378/65 |
| 2011/0293143 A1* | 12/2011 | Narayanan | G06T 7/0028 382/103 |
| 2012/0051664 A1* | 3/2012 | Gopalakrishnan | G06T 11/005 382/294 |
| 2013/0079626 A1* | 3/2013 | Shmatukha | A61B 6/03 600/420 |
| 2013/0287278 A1* | 10/2013 | Olivier | G06T 11/005 382/131 |
| 2014/0133717 A1* | 5/2014 | Kabus | A61B 6/5264 382/128 |
| 2015/0134261 A1* | 5/2015 | O'Connor | A61B 6/541 702/19 |
| 2015/0302613 A1* | 10/2015 | Hu | G06T 11/005 382/131 |
| 2016/0095565 A1* | 4/2016 | Fenchel | A61B 5/113 600/408 |
| 2016/0247293 A1* | 8/2016 | Beylin | G06T 11/005 |

OTHER PUBLICATIONS

Nehmeh, S. A., Erdi, Y. E., Rosenzweig, K. E., Schoder, H., Larson, S. M., Squire, O. D., & Humm, J. L. (2003). Reduction of respiratory motion artifacts in PET imaging of lung cancer by respiratory correlated dynamic PET: methodology and comparison with respiratory gated PET. Journal of Nuclear Medicine, 44(10), 1644-1648.*

Harteela, M., Hirvi, H., Mäkipää, A., Teuho, J., Koivumäki, T., Mäkelä, M. M., & Teräs, M. (2014). Comparison of end-expiratory respiratory gating methods for PET/CT. Acta Oncologica, 53(8), 1079-1085.*

Bloomfield, Peter M., et al. "The design and implementation of a motion correction scheme for neurological PET." Physics in Medicine & Biology 48.8 (2003): 959. (Year: 2003).*

Montgomery, Andrew J., et al. "Correction of head movement on PET studies: comparison of methods." Journal of Nuclear Medicine 47.12 (2006): 1936-1944. (Year: 2006).*

* cited by examiner

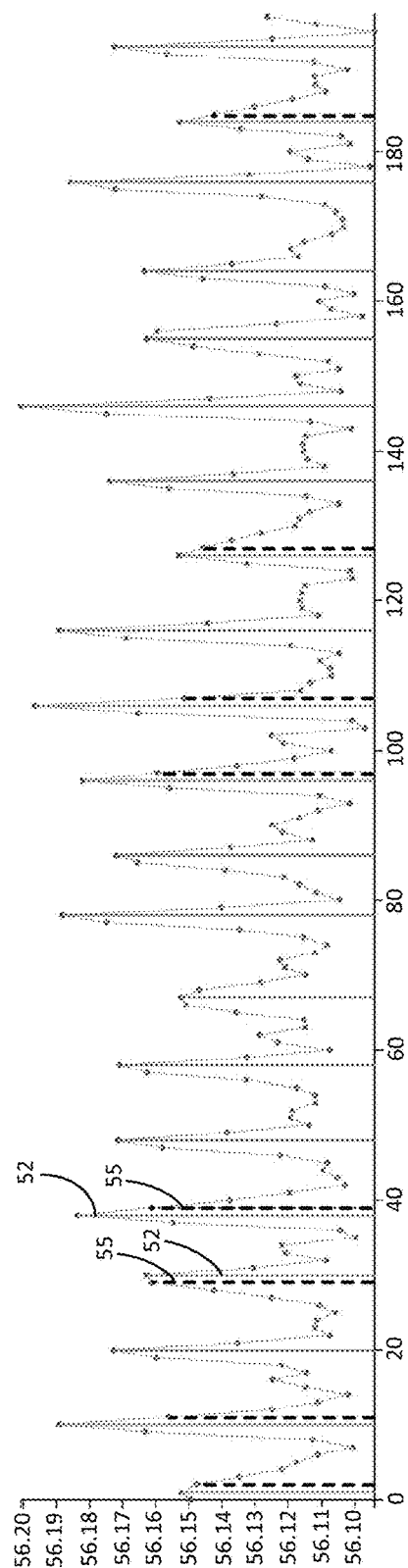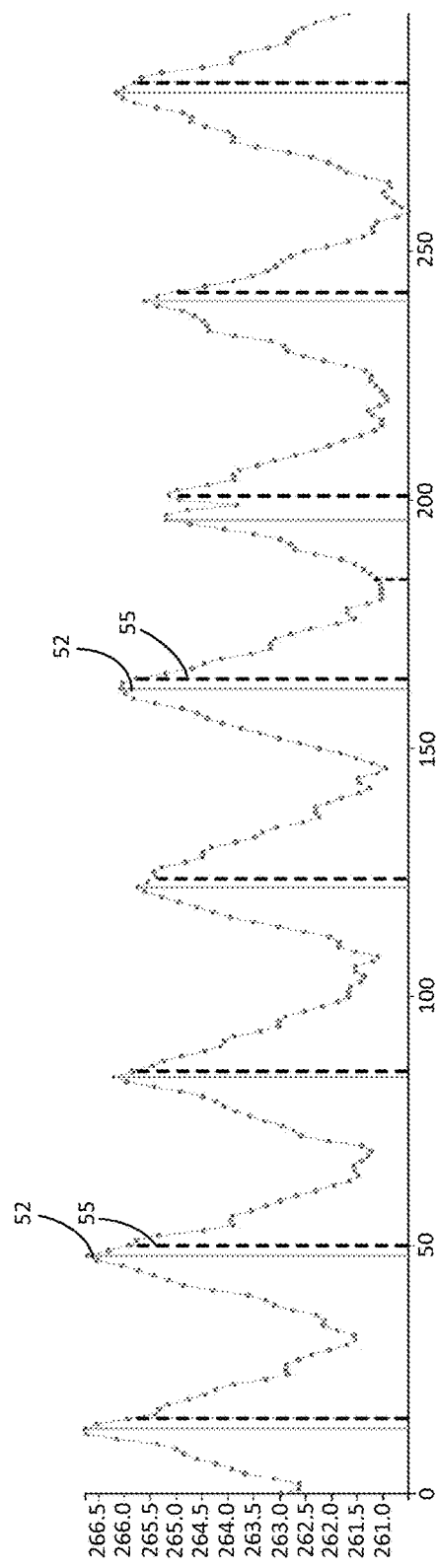

MOTION CORRECTION FOR PET MEDICAL IMAGING BASED ON TRACKING OF ANNIHILATION PHOTONS

CROSS-REFERENCE TO RELATED APPLICATION

The present application claims the benefit of U.S. Provisional application, Ser. No. 62/171,489, filed Jun. 5, 2015, entitled "MOTION CORRECTION FOR MEDICAL IMAGING," the disclosure of which is incorporated herein by reference in its entirety.

TECHNICAL FIELD

The present invention relates to motion correction in medical imaging systems.

BACKGROUND

Medical imaging systems/scanners (e.g., positron emission tomography (PET), computed tomography (CT), etc.) are typically used for diagnostic purposes. Patient movement during medical imaging, however, can result in degraded image quality and reduced diagnostic confidence. Two primary sources of patient movements are head and neck motion and respiratory motion.

Conventional solutions to correct for patient movement in medical imaging have significant drawbacks. One such technique consists of recording motion data from an electronic device attached to the patient (e.g., a waist band attached to the patient) to monitor the patient movement, while the patient is being scanned by the medical imaging scanner. Motion correction is performed through post-processing of the scanned data by correlating the scanned data with the motion data. In addition to the problems caused by the electronic hardware itself such as difficult placement on the patient, delays may be present between the scanned data and the motion data. Movement of the electronic device itself on the patient's body may occur during the scan. Another technique involves using a video monitoring system to detect the patient movement from a video recording of the patient during the scan. The motion data detected by this video monitoring system usually lacks accuracy, and patients find video recording of their medical examination intrusive. Thus, these motion correction methods not only are invasive and uncomfortable, but also result in inaccurate or erroneous motion correction of the scanned data.

SUMMARY

The present invention provides methods for motion correction for use in medical imaging systems. These methods require no attached electronic hardware devices or invasive camera systems, and offer high resolution tracking of motion that can automatically detect and correct patient movement during imaging.

In an embodiment, external emitting sources, such as positron emitting sources, are placed on the patient's head or neck in, at least, three off-axis positions. Annihilation photons produced by the external emitting sources may be detected by a medical imaging scanner and recorded among the listmode data of the medical imaging scanner. Listmode is a known data format for recording events, e.g., during a PET session. The listmode data may be used to determine the coincident lines of response corresponding to the annihilation photons from the external emitting sources. A coincident line of response, also known as a line of response (LOR) is an imaginary line connecting points where a pair of annihilation photons are detected by a medical imaging scanner. Thus, the locations and motion of the external emitting sources may be tracked in a three-dimensional space and recorded throughout the course of the scan. Static regions corresponding to subsequent locations of limited or no motion of the external emitting sources may be determined. Imaging data coinciding with the static regions are stored, while imaging data corresponding to transition regions from one static region to another are discarded. Motion vectors between each static region are recorded and then used in reconstruction to create a motion-corrected dataset. The listmode data may also be altered such that the motion affected events are repositioned into a common "motion free" geometry for use in subsequent histogramming and reconstruction.

In an embodiment, external emitting sources, such as positron emitting sources, are placed on the patient's torso along regions of motion associated with the patient's clinical indication, such as near the chest for lung imaging or just above the belly button for liver or gastric imaging. Annihilation photons produced by the external emitting sources may be detected by a medical imaging scanner and recorded among the listmode data of the medical imaging scanner. The listmode data may be used to determine the coincident lines of response corresponding to the annihilation photons from the external emitting sources. Thus, the locations and motion of the external emitting sources may be tracked and recorded throughout the course of the scan. Respiratory motion information may be derived from the tracked motion of the sources and a respiratory waveform may be generated. The respiratory waveform may be analyzed and marked for gating of the listmode data. Gating is a data processing technique applicable to listmode data, in which data that lies outside of specified "gate" areas are discarded. According to an embodiment, gating tags are subsequently inserted into the listmode data for histogramming and motion-corrected image reconstruction by the medical imaging scanner. The listmode data may also be altered such that the motion affected events are repositioned into a user defined "stationary" geometry for use in subsequent histogramming and reconstruction.

In an embodiment, an object of interest, such as a lesion, of the patient affected by respiratory or head and neck motion may be selected. A bounding region containing the object of interest may be identified. Listmode data of a medical imaging data may be used to determine the coincident lines of response measured within the bounding region. Thus, the locations and motion of the object of interest may be tracked. Respiratory motion information may be derived from the tracked motion of the object of interest and a respiratory waveform may be generated. The respiratory waveform may be analyzed and marked for gating of the listmode data. The gating tags are subsequently inserted into the listmode data for histogramming and motion-corrected image reconstruction by the medical imaging scanner. Head and neck correction information may also be derived from the tracked motion of the object of interest enabling the ability to identify periods of non-motion and remove motion-affected data. The listmode data may also be altered such that the motion affected events are repositioned into a common "motion free" geometry for use in subsequent histogramming and reconstruction.

BRIEF DESCRIPTION OF THE DRAWINGS

FIG. 5(a) illustrates exemplary respiratory waveforms for a preclinical subject.

FIG. 5(b) illustrates exemplary respiratory waveforms for a clinical subject.

DETAILED DESCRIPTION

Head and Neck Motion Correction

Figure 1:
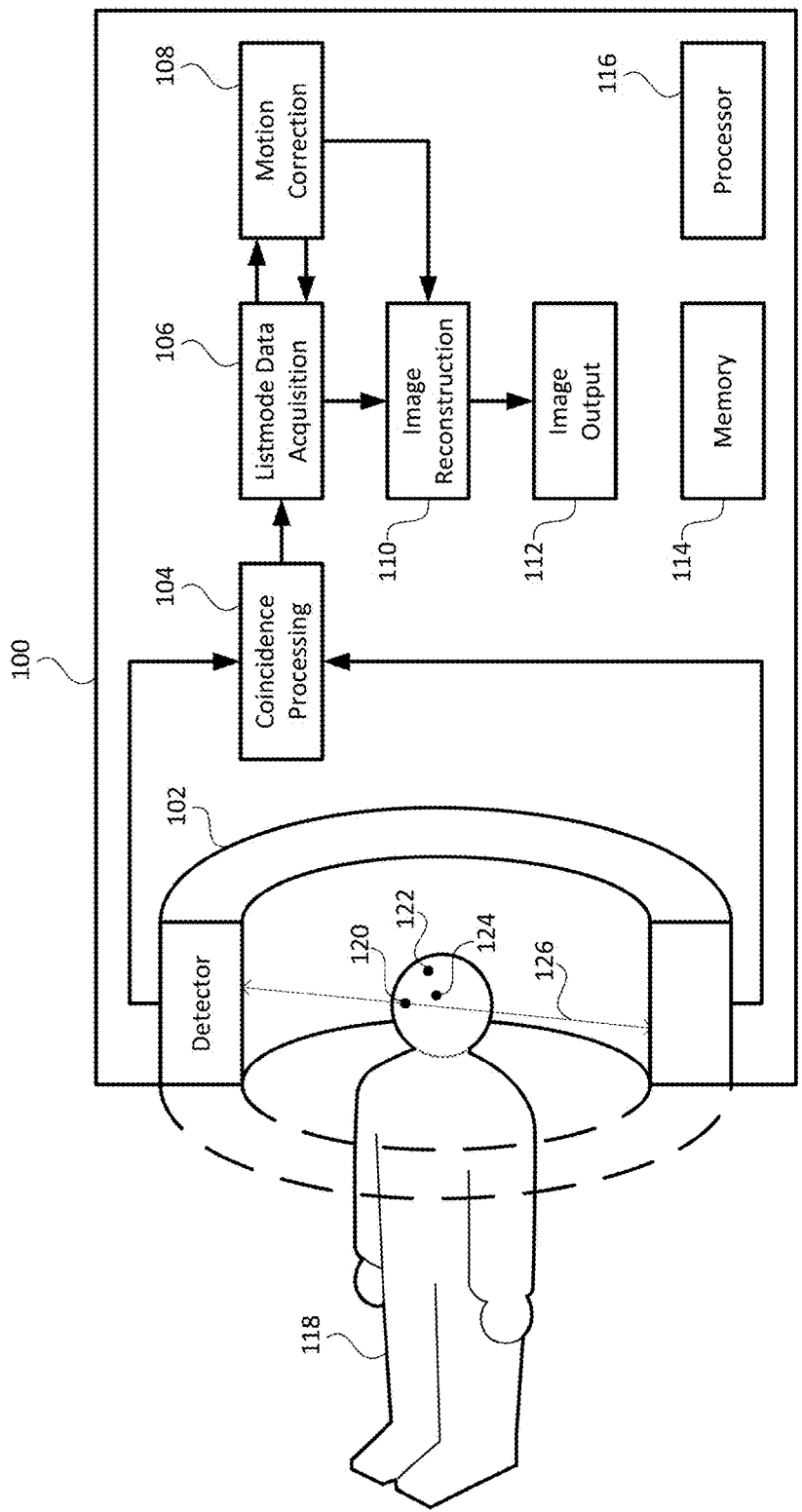
FIG. 1 illustrates a medical imaging system according to an embodiment of the present invention.

FIG. 1 illustrates a simplified diagram of a medical imaging system 100, according to an embodiment of the present invention. An example of the medical imaging system 100 may employ, but is not limited to, positron emission tomography (PET) or computed tomography (CT), or a combination thereof. The medical imaging system 100 may include a detector 102, a coincidence processing module 104, a listmode data acquisition module 106, a motion correction module 108, an image reconstruction module 110, an image output module 112, a memory 114, and a processor 116. A patient 118 may commonly be positioned within the detector 102, as shown in FIG. 1, and may be moved horizontally depending on the region of interest of the patient's body that needs to be scanned. For continuous bed motion enabled systems, the patient may be moved continually through the horizontal scan range.

The memory 114 may be provided as a volatile memory, a non-volatile memory, or a combination thereof. The memory 114 may store program instructions, scan data generated by the medical imaging system 100, and any data as needed by the medical imaging system 100. Algorithms to operate the coincidence processing module 104, the listmode data acquisition module 106, the motion correction module 108, the image reconstruction module 110, and the image output module 112 may be provided as software stored in the memory 114. The processor 116 may be a microcontroller or a microprocessor. The processor 116 may execute the instructions stored in the memory 114 and may control the operations of the coincidence processing module 104, the listmode data acquisition module 106, the motion correction module 108, the image reconstruction module 110, and the image output module 112.

In another embodiment, the motion correction module 108 may be coupled externally to the medical imaging system 100. In such an embodiment, the motion correction module 108 may include a separate memory and processor.

Figure 2:
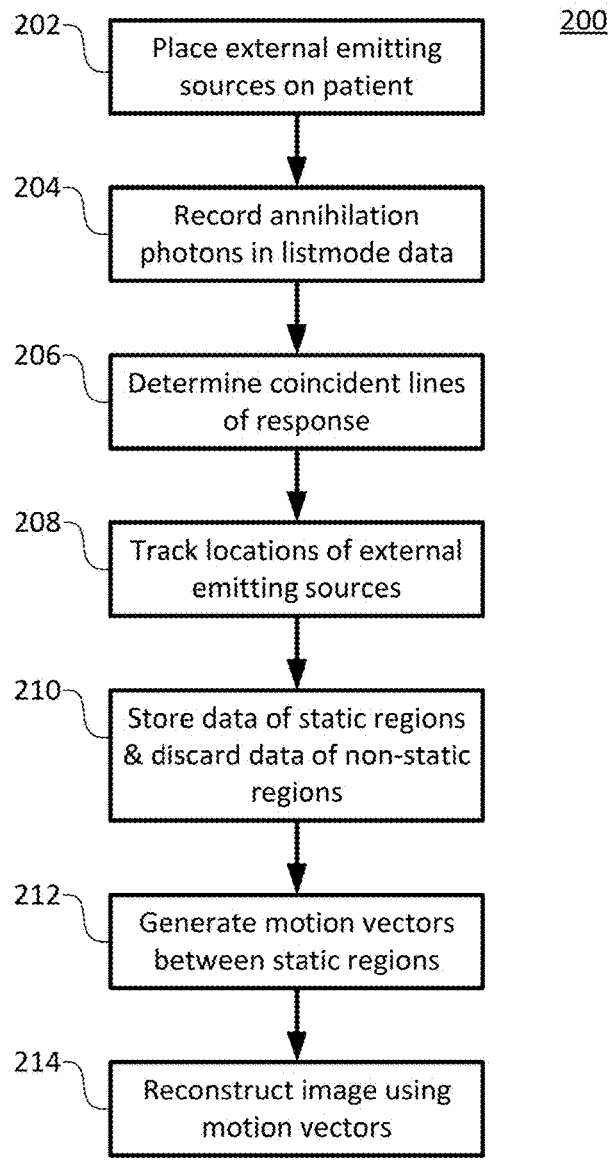
FIG. 2 illustrates a method for head and neck motion correction in medical imaging, according to an embodiment of the present invention.

FIG. 2 illustrates a method 200 for head and neck motion correction in medical imaging, according to an embodiment of the present invention.

In step 202, external emitting sources, such as positron emitting sources, are placed on the patient's head or neck in three off-axis positions, as shown by positions 120, 122, and 124 in FIG. 1, for example.

In step 204, pairs of annihilation photons produced by the external emitting sources and moving in approximately opposite directions may be detected by detector 102 and recorded among the listmode data acquired by the listmode data acquisition module 106 of the medical imaging system 100. For example, the listmode data may be in 64-bit listmode format.

In step 206, the motion correction module 108 may use the listmode data from the listmode data acquisition module 106 to determine the coincident lines of response from the coincidence processing module 106 corresponding to pairs of annihilation photons from the external emitting sources. FIG. 1 shows an example of a coincident line of response 126.

In step 208, from the corresponding coincident lines of response, the motion correction module 108 may track the locations of the external emitting sources at positions 120, 122, and 124 in a three-dimensional space and record these locations throughout the course of the scan.

In step 210, the motion correction module 108 may determine static regions corresponding to subsequent locations of limited or no motion of the external emitting sources. The motion correction module 108 stores imaging data coinciding with the static regions and discards imaging data corresponding to transition regions from one static region to another. Imaging data may be any data among the listmode data that do not correspond to pairs of annihilation photons from the external emitting sources.

In step 212, the motion correction module may generate motion vectors between each static position.

In step 214, the image reconstruction module 112 may use the motion vectors to create a motion-corrected dataset, thereby reconstructing an image.

One skilled in the art would appreciate that, given that motion correction may be performed on the raw listmode data prior to image reconstruction, the head and neck motion correction techniques described herein may be applied to many PET imaging systems.

The head and neck motion correction techniques described herein were tested in an experimental setup similar to the one shown in FIG. 1. A plurality of patients were imaged on a PET/CT scanner, i.e., the medical imaging system 100. Low activity/dose point sources were placed on the heads of the patients, in asymmetrical locations to enable three-dimensional tracking, as illustrated by positions 120, 122, and 124 in FIG. 1, for example. The patients were instructed to move during their scans, simulating typical patient movements during imaging. For each patient, the PET/CT scanner acquired PET data for 10 minutes in a 64-bit listmode format. A motion correction module 108 used algorithms, as outlined in steps 206 and 208 above, to track head motions during the scans. As in step 210, the motion correction module 108 corrected data by calculating centroid locations for each source at time points when the patient was still. Events associated with transitional motion were discarded. The initial CT position was used as the reference position. Subsequent static positions were transformed to the reference frame by calculating transformation matrices from the calculated centroid locations. All reoriented static positions were summed to create the final dataset.

As an alternative to using a CT position as a reference, other anatomical modalities may be used to generate a reference point for which the transformation matrix may be generated. For instance, the list mode data itself may be used to generate one or more reference points for the reconstruction of three-dimensional volumes from specific time segments within the acquired list mode data. Thus, an alternative reconstruction process may involve segmenting the list mode data, designating specific segments as corresponding to "stationary" geometries, reconstructing a three-dimensional volume for those designated segments, then combining the reconstructed volumes into a single volume.

Figure 3:
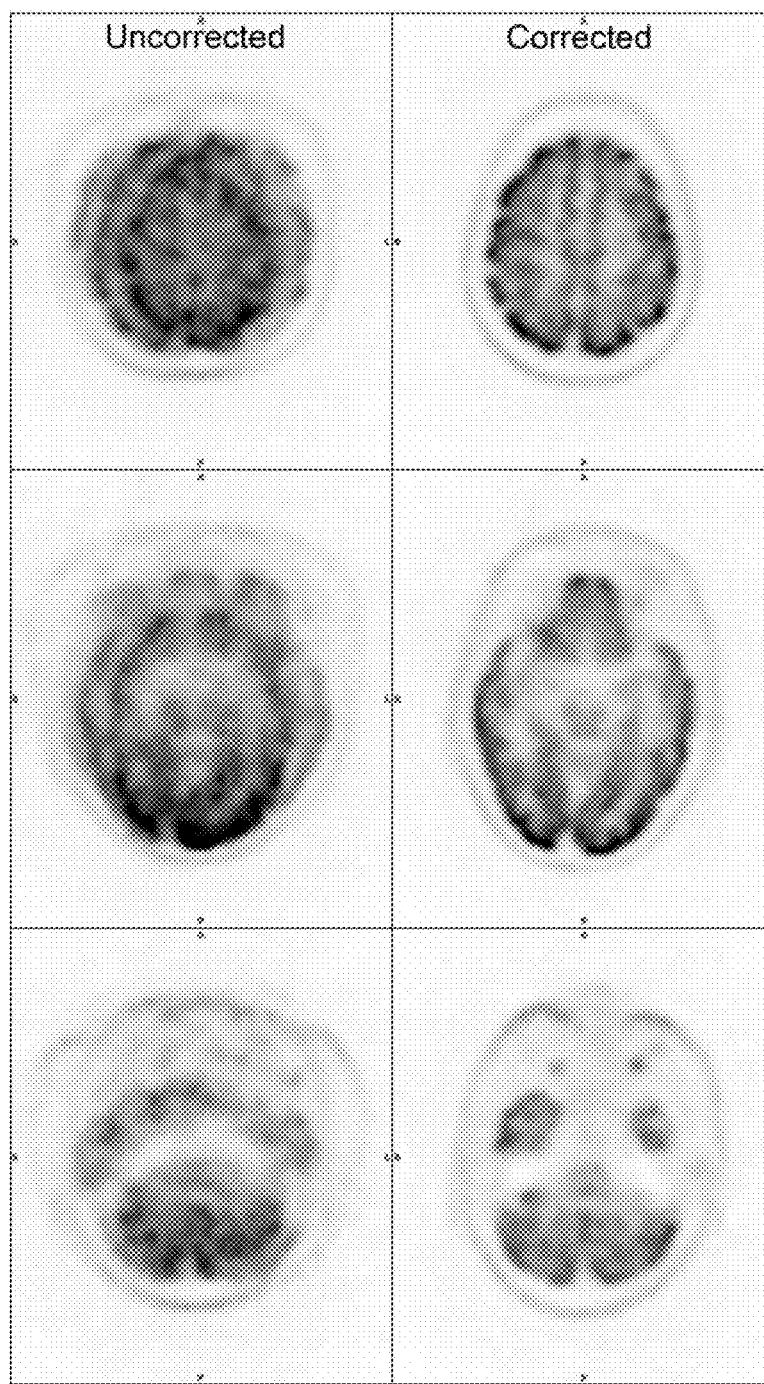
FIG. 3 compares images from a dataset that has been corrected for head and neck motion to images from an uncorrected dataset.

FIG. 3 illustrates a sample of images resulting from the experiment. FIG. 3 shows, on the left, images resulting from a dataset that has not been motion-corrected. The images on the right result from the same, but motion-corrected, dataset.

Analysis of the images indicated that patient motion during the scan severely degraded the quality of the images. Key features of the brain are hardly discernible. The algorithms used by motion correction module 108 successfully tracked all three source positions during the scan. Following the motion correction, the images of the brain were crisp with no signs of motion, as shown on the right side of FIG. 3. In addition, this head and neck motion correction method 200 enabled recovery of about 97% of data. Therefore, head and neck motion correction method 200 is a robust method for automatic motion correction in head and neck patients. Automatic correction of motion may prevent inaccurate radiological examinations and prevent burdening patients with repeated imaging procedures.

Respiratory Motion Correction—with External Emitting Sources

Respiratory motion in medical imaging affects diagnostic image quality for a wide range of cancers, including: lung, liver, pancreatic, and gastric. The medical imaging system 100 shown in FIG. 1 may also be used for respiratory motion correction. However, the external emitting sources are placed on the patient's torso along regions of motion associated with the patient's clinical indication, such as near the chest for lung imaging or just above the belly button for liver or gastric imaging. The torso of the patient 118 must be positioned within detector 102 accordingly or pass through the axial field of view during the course of data acquisition.

Figure 4:
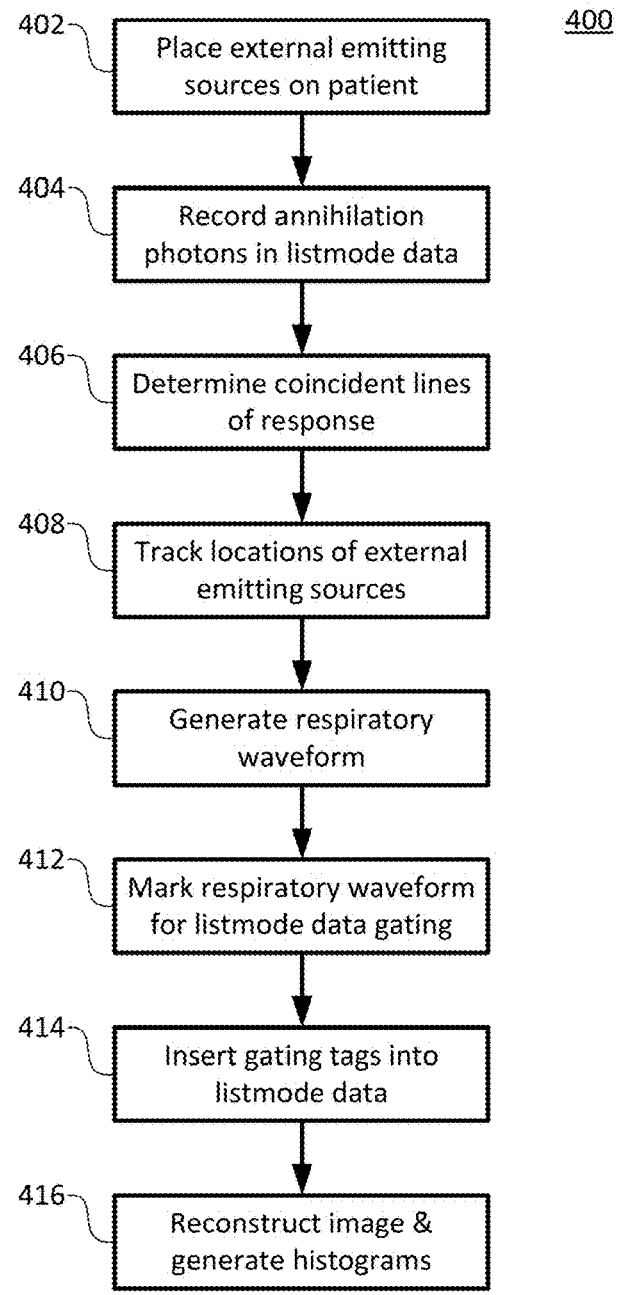
FIG. 4 illustrates a method for respiratory motion correction in medical imaging, according to an embodiment of the present invention.

FIG. 4 illustrates a method 400 for respiratory motion correction in medical imaging, according to an embodiment of the present invention.

In step 402, external emitting sources, such as positron emitting sources, are placed on the on the patient's torso along regions of motion associated with the patient's clinical indication, such as near the chest for lung imaging or just above the belly button for liver or gastric imaging.

In step 404, pairs of annihilation photons produced by the external emitting sources and moving in approximately opposite directions may be detected by detector 102 and recorded among the listmode data acquired by the listmode data acquisition module 106 of the medical imaging system 100.

In step 406, the motion correction module 108 may use the listmode data from the listmode data acquisition module 106 to determine the coincident lines of response from the coincidence processing module 106 corresponding to pairs of annihilation photons from the external emitting sources. FIG. 1 shows an example of a coincident line of response 126.

In step 408, from the corresponding coincident lines of response, the motion correction module 108 may track the locations of the external emitting sources and record these locations throughout the course of the scan.

In step 410, the motion correction module 108 may derive respiratory motion information from the tracked motion of the sources and generate a respiratory waveform.

In step 412, the motion correction module 108 may analyze and mark the respiratory waveform for gating of the listmode data.

In step 414, the motion correction module may insert gating tags into the listmode data.

In step 416, based on the gating tags, the image reconstruction module 112 may reconstruct a motion-corrected image using the inserted gating tags and generate histograms. For example, as noted below, the gating tags may mark locations of local maxima for each respiratory cycle, enabling reconstruction through amplitude or phase-based gating.

One skilled in the art would appreciate that, given that motion correction may also be performed on the raw listmode data prior to image reconstruction, the respiratory motion correction techniques described herein may be applied to many PET imaging system.

The respiratory motion correction techniques described herein were tested in both preclinical and clinical imaging systems. For both systems, low activity/dose point sources were placed on animals or humans in sites of respiratory motion for software tracking by the motion correction module 108. Standard electronic gating systems were also attached to the subjects with a respiratory pad used for mouse imaging and a respiratory band used for human imaging. PET data were collected for 10 minutes for clinical and preclinical subjects. 64-bit listmode data was acquired with tags inserted from standard electronic systems. The raw listmode data was processed by the motion correction module 108, as discussed above, inserting the gating tags into the listmode data. The motion correction module 108 was configured to insert gating tags at local maxima in the y-axis for each respiratory cycle. High frequency noise was removed by applying a discrete wavelet transformation denoising technique. Amplitude-based gating was used to reconstruct static images with a duty cycle of 20%. It should be noted that phase-based gating may also be used for the image reconstruction.

FIGS. 5(a) and 5(b) illustrate exemplary respiratory waveforms for a preclinical subject and a clinical subject, respectively. The waveforms are marked for gating tags. The solid vertical marks, some of which are labeled 52, correspond to tags to be inserted into the listmode data by the respiratory motion correction method 400, while the broken vertical marks, some of which are labeled 55, correspond to tags from the standard electronic gating system. Comparison of waveforms between electronic and software-based gating indicated correlation between insertion points of greater than 99%, while timing drift in gating tag entry was only observed in the electronic signals generated by the standard electronic gating system.

Figure 6:
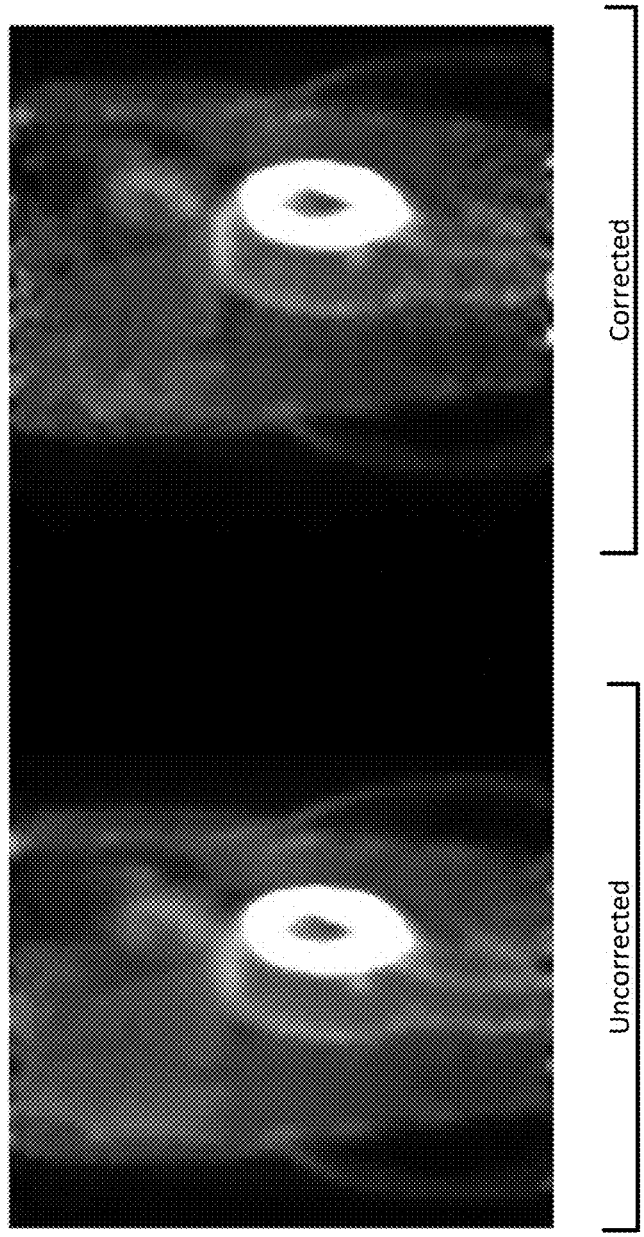
FIG. 6 compares an image from a dataset that has been corrected for respiratory motion to an image from an uncorrected dataset.

FIG. 6 illustrates exemplary images resulting from the experiment. FIG. 6 shows, on the left, an image resulting from a dataset that has not been motion-corrected, and, on the right, a corresponding image resulting from the same, but motion-corrected, dataset.

Phase-based and amplitude-based gated reconstructions are possible using this respiratory motion correction method 400 and shows improved image quality in regions of respiratory motion. Therefore, the respiratory motion correction method 400 is able to produce accurate respiratory waveforms and correct insertion of gating tags. Visual comparison of data indicates that reconstructed images using tags inserted from the respiratory motion correction method 400 produce images with reduced motion artifacts.

Motion Correction without External Emitting Sources

Figure 7:
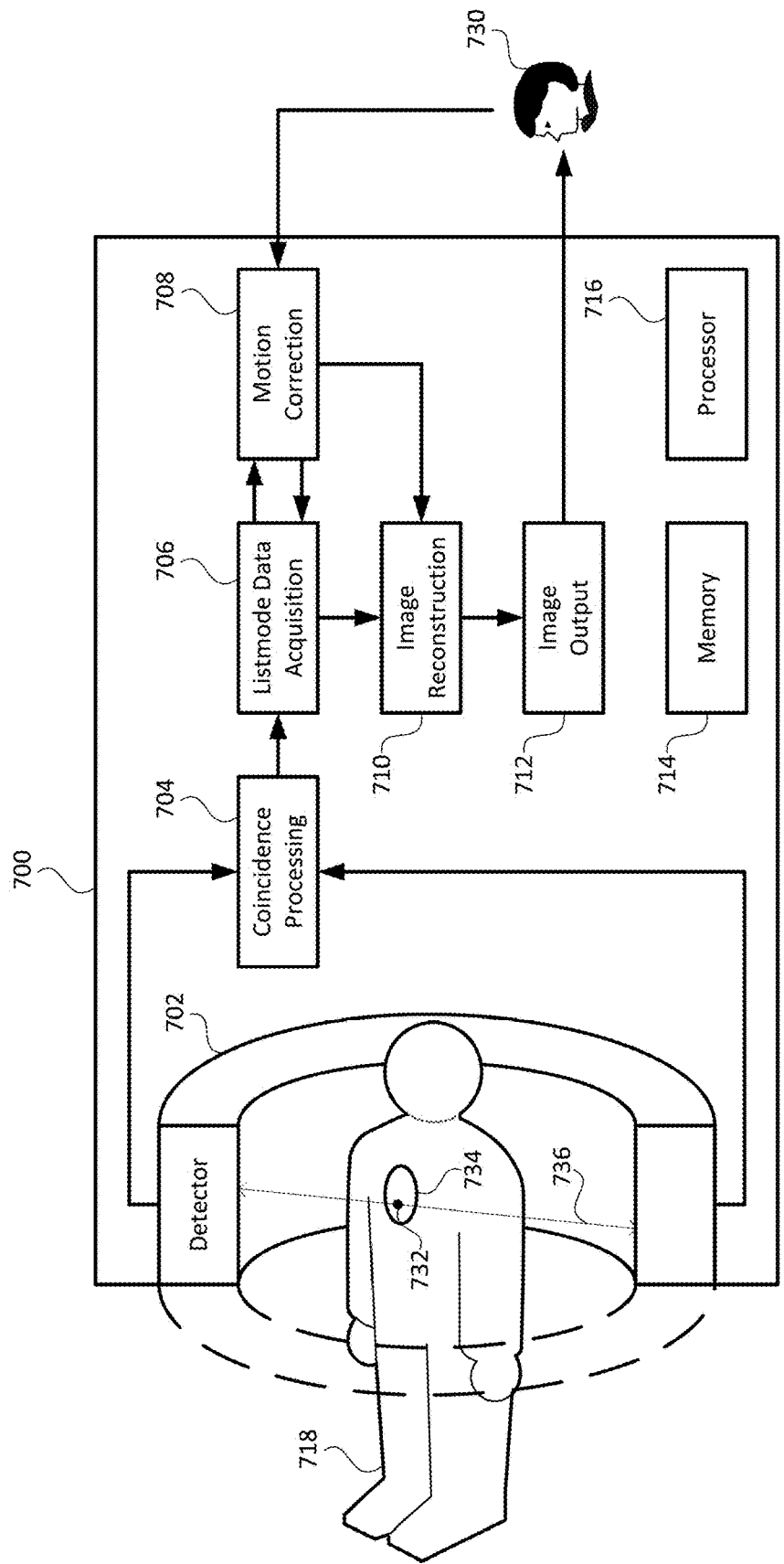
FIG. 7 illustrates a medical imaging system according to an embodiment of the present invention.

Respiratory or head and neck motion correction may also be realized without the use external emitting sources. FIG. 7 illustrates a simplified diagram of a medical imaging system 700, according to an embodiment of the present invention. An example of the medical imaging system 700 may employ, but is not limited to, positron emission tomography (PET) or computed tomography (CT), or a combination thereof. The medical imaging system 700 may include a detector 702, a coincidence processing module 704, a listmode data acquisition module 706, a motion correction module 708, an image reconstruction module 710, an image output module 712, a memory 714, and a processor 716. A patient 718 may commonly be positioned within the detector 702, as shown in FIG. 7, and may be moved horizontally depending on the region of interest of the patient's body that needs to be scanned. For continuous bed motion enabled systems, the patient 718 may be moved continually through the horizontal scan range. A user 730 may interact with the medical imaging system 700 to select an object of interest 732, the location of which needs to be tracked, as will be explained in more details below. Examples of the object of interest 732 may be, but are not limited to, a lesion in the lung and edges of anatomical surfaces, such as the dome of the liver.

Figure 8:
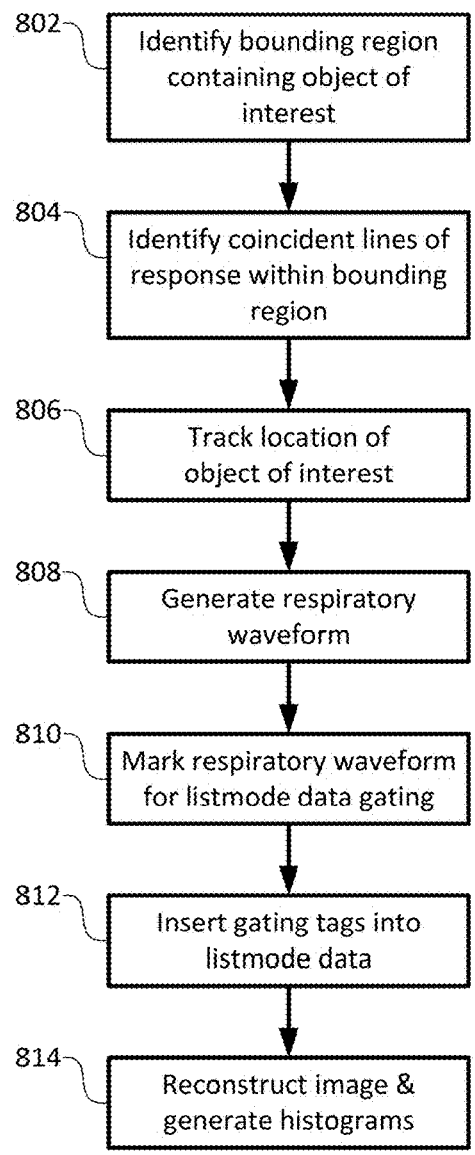
FIG. 8 illustrates a method for respiratory motion correction in medical imaging without the use of external emitting sources, according to an embodiment of the present invention.

FIG. 8 illustrates a method 800 for respiratory motion correction in medical imaging without the use of external emitting sources, according to an embodiment of the present invention.

In step 802, using a reconstructed image from the image output module 712, the user 730 may select an object of interest 732, such as a lesion, of the patient affected by respiratory or head and neck motion. The user 730 may then identify a bounding region 734 containing the object of interest 732. FIG. 7 illustrates, for example, an object of interest 732 bounded by a bounding region 734.

In step 804, the motion correction module 708 may use the listmode data from the listmode data acquisition module 706 to identify the coincident lines of response, from the coincidence processing module 706, measured within the bounding region 734. FIG. 7 shows an example of a coincident line of response 736.

In step 806, from the identified coincident lines of response, the motion correction module 708 may track the location of the object of interest 732 throughout the course of the scan.

In step 808, the motion correction module 708 may derive respiratory motion information from the tracked motion of the object of interest 732 and generate a respiratory waveform.

In step 810, the motion correction module 708 may analyze and mark the respiratory waveform for gating of the listmode data.

In step 812, the motion correction module may insert gating tags into the listmode data.

In step 814, based on the gating tags and using either amplitude-based gating or phase-based gating, the image reconstruction module 712 may reconstruct a motion-corrected image and generate histograms.

One skilled in the art would appreciate that, given that motion correction may be performed on the raw listmode data prior to image reconstruction, the respiratory motion correction techniques described herein may be applied to many PET imaging systems.

The foregoing description has been set forth merely to illustrate the invention and is not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method for correcting motion during medical imaging, the method comprising:
   tracking annihilation photons produced by one of (i) external emitting sources placed onto a body of a person being imaged or (ii) an object of interest in the body, wherein said tracking includes tracking all coincident lines of response detected at a detector element, in medical imaging data, wherein each coincident line of response corresponds to a pair of annihilation photons detected at connecting points of the coincident line of response;
   generating motion information based on the tracking of each of said coincident lines of response, wherein the motion information includes motion vectors between static regions corresponding to locations of limited or no motion; and
   forming a motion-corrected image from recorded image data using the motion information.

2. The method of claim 1 further comprising:
   discarding portions of the recorded image data that are associated with non-static regions.

3. The method of claim 1, wherein the motion-corrected image is formed by transforming the static regions to a reference position.

4. The method of claim 3, wherein annihilation photons produced by the external emitting sources are tracked, and wherein the transforming includes calculating transformation matrices from centroid locations of the external emitting sources.

5. The method of claim 1, wherein annihilation photons produced by the object of interest are tracked, and wherein the object of interest is a lesion or an edge of an anatomical surface.

6. A system for correcting motion during medical imaging, the system comprising:
   a detector device that tracks annihilation photons produced by one of (i) external emitting sources placed onto a body of a person being imaged or (ii) an object of interest in the body, wherein tracking includes tracking all coincident lines of response detected at a detector element, in medical imaging data, wherein each coincident line of response corresponds to a pair of annihilation photons detected at connecting points of the coincident line of response; and
   a hardware processor that generates motion information based on the tracking of each of said coincident lines of response, and forms a motion-corrected image from raw line of response data using the motion information, wherein the motion information includes motion vectors between static regions corresponding to locations of limited or no motion.

7. The system of claim 6, wherein the processor discards portions of the raw line of response data that are associated with non-static regions.

8. The system of claim 6, wherein the processor forms the motion-corrected image by transforming the static regions to a reference position.

9. The system of claim 8, wherein the detector device tracks annihilation photons produced by the external emitting sources, and wherein the transforming includes calculating transformation matrices from centroid locations of the external emitting sources.

10. The system of claim 6, wherein the detector device tracks annihilation photons produced by the object of interest, and wherein the object of interest is a lesion or an edge of an anatomical surface.

\* \* \* \* \*